United States Patent [19]

Ikeda et al.

[11] Patent Number: 5,493,056
[45] Date of Patent: Feb. 20, 1996

[54] METHOD OF PRODUCING TETRAKIS (PENTAFLUOROPHENYL) BORATE DERIVATIVES USING PENTAFLUOROPHENYL ALKALI METAL SALT PREPARED FROM PENTAFLUOROBENZENE

[75] Inventors: Yoshihiko Ikeda, Shinnanyo; Takeo Yamane, Ogori; Eiichi Kaji; Kenji Ishimaru, both of Shinnanyo, all of Japan

[73] Assignee: Tosoh Akzo Corporation, Tokyo, Japan

[21] Appl. No.: 171,174

[22] Filed: Dec. 22, 1993

[30] Foreign Application Priority Data

Dec. 28, 1992 [JP] Japan .................................. 4-361478
Dec. 28, 1992 [JP] Japan .................................. 4-361479

[51] Int. Cl.$^6$ .................................................... C07C 5/02
[52] U.S. Cl. .................................................... 568/6
[58] Field of Search .................................................... 568/6

[56] References Cited

U.S. PATENT DOCUMENTS

3,311,662  3/1967  Washburn et al. .................. 260/606.5

OTHER PUBLICATIONS

Harper et al., *J. Organic Chemistry*, vol. 29, pp. 2385–2389, 1964 "Reactions of Organometallics with Fluoroaromatic Compounds".

Kobayashi et al, *Chem. Abstracts*, vol. 100, No. 17, p. 660, 1984; AN139179s, "Synthesis of Trifluoromethylated Tetraphenylborates . . . ".

Massey et al, *Chem. Abstracts*, vol. 59, No. 8, 1963; AN 8771b; "Tris(Penta Fluorophenyl)Boron".

Journal of Organometallic Chemistry, vol. 2, 1964, A. G. Massey, et al., "Perfluorophenyl Derivatives of the elements I. Tris(Pentafluorophenyl)Boron", pp. 245–250.

*Primary Examiner*—Gary L. Geist
*Assistant Examiner*—Joseph D. Anthony
*Attorney, Agent, or Firm*—Oblon, Spivak, McClelland, Maier, & Neustadt

[57] ABSTRACT

The invention relates to a method for producing tetrakis(pentafluorophenyl)borate derivatives of the formula $(C_6F_5)_4BM$ which comprises reacting 1 equivalent of pentafluorobenzene with 0.5 to 1.5 equivalents of an organometallic compound RM at $-120°$ to $80°$ C., in an ether type solvent, a hydrocarbon type solvent or a mixture thereof, to generate pentafluorophenyl alkali metal salt represented by the formula $C_6F_5M$, and then reacting either (1) not less than 3.7 equivalents of said pentafluorophenyl alkali metal salt with 1 equivalent of a boron compound $BX_3$, or (2) not less than 0.8 equivalents of said pentafluorophenyl alkali metal salt with 1 equivalent of tris(pentafluorophenyl)borane.

2 Claims, No Drawings

METHOD OF PRODUCING TETRAKIS (PENTAFLUOROPHENYL) BORATE DERIVATIVES USING PENTAFLUOROPHENYL ALKALI METAL SALT PREPARED FROM PENTAFLUOROBENZENE

BACKGROUND OF THE INVENTION

The present invention relates to a novel method of production of tetrakis(pentafluorophenyl)borate derivatives using pentafluorobenzene.

The boron derivative obtainable according to the invention is a very useful substance as an intermediate of a co-catalyst for cationic complex polymerization.

In recent years, scientific literature or patents on studies, in which a cationic complex is generated using tetrakis(pentafluorophenyl)borate derivatives and cyclopentadienyl transition metal complex, so-called metallocene derivatives, and this is used as a catalyst for the polymerization reaction, have increased remarkably. For example, Macromol. Chem. Rapid Commun., A, p.p. 663–667 (1991) etc. are available. However, for the production of tetrakis(pentafluorophenyl)borate derivatives, relatively expensive bromopentafluorobenzene has been used conventionally as a starting substance for the source of pentafluorophenyl group.

In one method bromopentafluorobenzene entered into a bromine-metal exchange reaction using organometallic compounds such as butyllithium to generate pentafluorophenyllithium, which was then reacted with boron trichloride, boron trifluoride, or the like as a starting raw material for the source of boron to synthesize directly. In another method, bromopentafluorobenzene was reacted with magnesium to generate a Grignard reagent such as pentafluorophenylmagnesium bromide, which was then reacted with boron trichloride, boron trifluoride, or the like similarly as a starting raw material for the source of boron to synthesize tris(pentafluorophenyl)borane, and this was further reacted with pentafluorophenyllithium to produce tetrakis(pentafluorophenyl)borate derivatives (J. Organometallic Chem., 2, 245–250 (1964)).

Bromopentafluorobenzene is obtained by brominating pentafluorobenzene. If it is possible to directly produce tetrakis(pentafluorophenyl)borate derivatives from pentafluorobenzene, then the production processes can be reduced by one process, leading to easy availability and also decreased price of a starting raw material. Moreover, literature, in which pentafluorophenyllithium or pentafluorophenylmagnelium bromide is generated using pentafluorobenzene as a starting raw material and this is used for reaction, have already been presented (J. Chem. Soc., 166 (1959), Synthesis of Fluoroorganic Compounds, p141, J. Org. Chem. 29, 2385 (1964) and ibid, 31, 4229 (1966)), but application to the production of tetrakis(pentafluorophenyl)borate derivatives is not made.

In view of the above, the inventors investigated extensively a synthetic method without using relatively expensive bromopentafluorobenzene as a starting raw material by changing the use of bromopentafluorobenzene to that of pentafluorobenzene as a starting substance for the production of tetrakis(pentafluorophenyl)borate derivatives and eliminating the brominating process of pentafluorobenzene, leading to the invention.

SUMMARY OF THE INVENTION

The gist of the invention lies in a production method, wherein, with 1 equivalent of pentafluorobenzene represented by the formula $C_6HF_5$ (I), 0.5 to 1.5 equivalents of organometallic compound represented by the molecular formula RM (II), wherein M denotes an alkali metal ion, R denotes a hydrocarbon group with carbon atoms of 1 to 10 and the said hydrocarbon group may contain functional groups having no influence on the reaction, are reacted at −120° C. to 80° C. in an ether type solvent, a hydrocarbon type solvent or a mixed solvent of the ether type solvent with the hydrocarbon type solvent to generate pentafluorophenyl alkali metal salt represented by the molecular formula $C_6F_5M$ (III), wherein M denotes an alkali metal ion, and then, with 1 equivalent of a boron compound represented by the molecular formula $BX_3$ (IV), wherein X denotes a halogen atom not less than 3.7 equivalents of pentafluorophenyl metal compound represented by the formula [III] are reacted to produce tetrakis(pentafluorophenyl)borate derivatives represented by the molecular formula $(C_6F_5)_4BM$ (VII), or a production method, wherein, with 1 equivalent of pentafluorobenzene represented by the formula (I), 0.5 to 1.5 equivalents of organometallic compound represented by the chemical formula RM (II), wherein M and R are defined as above, are reacted at −120° C. to 80° C. in an ether type solvent, hydrocarbon type solvent or a mixed solvent of the ether type solvent with the hydrocarbon type solvent to generate pentafluorophenyl alkali metal salt represented by the formula (III), and then, with 1 equivalent of tris(pentafluorophenyl)borane represented by the molecular formula $(C_6F_5)_3B$ (VIII), not less than 0.8 equivalents of pentafluorophenyl metal compound represented by the formula $C_6F_5M$ (III), wherein M denotes an alkali metal ion, are reacted to produce tetrakis(pentafluorophenyl)borate derivatives represented by the formula (VII), wherein M denotes an alkali metal ion.

DETAILED DESCRIPTION OF THE INVENTION

The invention is further illustrated below.

The ether type solvents include diethyl ether, dipropyl ether, diisopropyl ether. dibutyl ether, diisoamyl ether, 1,2-dimethoxyethane, 1,2-diethoxyethane, di-2-methoxyethyl ether, tetrahydrofuran, tetrahydropyran, 1,4 -dioxane, etc.

Next, the hydrocarbon type solvents include indicate saturated hydrocarbons such pentans, isopentane, hexane, cyclohexane, haptans, octane. nonane, decshe. undocane, dodecane, tridecane, tetradecane, pentadecane. hexadecane, n-paraffin and petroleum ether. aromatic hydrocarbons such as benzene, toluene, o-xylene, m-xylene, p-xylene, 1,2.3-trimethylbenzene, 1,2,4-trimethylbenzene, 1,2,5-trimethylbenzene. 1,3,5-trimethylbenzene, ethylbenzene, propylbenzene and butylbenzene, and mixtures thereof.

Next, the functional groups having no influence on the reaction in the formula (II) include methyl group, ethyl group, propyl group, isopropyl group, propenyl group, 2-isopropenyl group, allyl group, butyl group, sec-butyl group, tert-butyl group, isobutyl group, pentyl group, sec-pentyl group, tert-pentyl group, neo-pentyl group, isopentyl group, sec-isopentyl group, hexyl group, lec-hexyl group, isohexyl group, sec-isohexyl group, cyclohexyl group, phenyl group, benzyl group, o-tolyl group, m-tolyl group, p-tolyl group, methoxymethyl group, methylthiomethyl group, 2-dimethylaminoethyl group, o-anisyl group, m-aniyl group, p-anisyl group, trimethylsilylmethyl group, etc., and examples of organometallic compounds represented by the formula (II) include methyllithium, ethyllithium, propyllithium, isopropyllithium, butyllithium, isobutyllithium, sec-butyllithium, tert-butyllithium, pentyllithium. isopentyllithium, sec-pentyllithium, tert-pentyllithium, sec-isopentyllithium, hexyllithium, isohexyllithium, sec-hexyliithium, cyclohexyllithium, phenyllithium, o-tolyllithium. m-tolyllithium, p-tolyllithium, trimethyleilyllithium, phenylmodium, o-tolylsodium, m-tolyleodium, p-tolylsodium, butyllithium/potassium-tert-butoide, butyllithium/sodium-tert-butoxide etc., and isopropyllithium, secbutyllithium, tert-butyllithium, sec-pentyllithium, tertpentyllithium, sec-isopentyllithium, sec-hexyllithium, cyclohexyllithium, etc. which are strong in basicity and hard to influence on the reaction, are preferable.

Examples of boron compounds represented by the formula (IV) are boron trifluoride, boron trichloride, boron tribromide, boron trifluoride, trimethyl borate, triethyl borate, tripropyl borate, triisopropyl borate, tributyl borate, trimethyleneborate, tris(dimethylamino)borate, tris(diethylamino)borate, tripyrrolidinoborate, tripiperidinoborate, trimorpholinoborate, et. are mentioned. In addition, complexes such as boron trifluoride-diethyl ether complex, boron trifluoride-dibutyl ether complex, boron trifluoride-dimethyl sulfide complex, boron trichloride-diethyl ether complex and boron trichloride-dibutyl ether complex are also included in this category.

The production method is illustrated below in sequence.

Pentafluorobenzene represented by the formula $C_6HF_5$ is dissolved into an ether type solvent, a hydrocarbon type solvent or a mixed solvent thereof. With this solution, 0.5 to 1.5 equivalents of the organometallic compound represented by the formula RM, wherein M denotes an alkali metal ion, R denotes a hydrocarbon group with carbon atoms of 1 to 10, per 1 equivalent of pentafluorobenzene are reacted within a range from −120° to 80° C.

In this reaction, when generating pentafluorophenyl alkali metal salt represented by the formula $C_6F_5M$, if the amount of organometallic compound represented by the formula RM is much less than the amount of pentafluorobenzene represented by the formula $C_6HF_5$, then a lot of unreacted pentafluorobenzene remains, and, if an excess amount of organometallic compound is used, then there is a fear of a halogen-metal exchange reaction with fluorine of the pentafluorophenyl metal salt produced and represented by the formula $C_6F_5M$. Hence, it is preferable to use 0.8 to 1.20 equivalents of the organometallic compound represented by the formula RM. If the reaction temperature is lower than −80° C., the reaction proceeds extremely slowly, while if it is higher than 0 ° C., side reactions proceed extremely rapidly, thus resulting in very low yield in both cases. Hence, it is desirable to conduct the reaction in a range of −80° to 0° C. The reaction mixture is allowed to react for 5 to 120 minutes at the same temperature, whereby pentafluorophenyl alkali metal salt represented by the formula $C_6F_5M$ is prepared.

Pentafluorophenyl alkali metal salt produced herein and represented by the formula $C_6F_5M$ is $C_6H_5Li$, $C_6H_5Na$ or $C_6H_5K$.

Although the use level of pentafluorophenyl alkali metal salt is 4 equivalents as a theoretical amount when using the boron compound represented by the formula [IV] for the reaction, the decrease in the yield of tetrakis(pentafluorophenyl)borate derivatives becomes remarkable in the case of less than 3.7 equivalents, hence a use of not less than 3.7 equivalents is desirable.

Moreover, when using tris(pentafluorophenyl)borane for the reaction as a boron compound, the theoretical amount is 1 equivalent, but the decrease in the yield of tetrakis(pentafluorophenyl)borate derivatives is remarkable in the case of less than 0.7 equivalents shown here, hence use of not less than 0.7 equivalents is desirable.

As for the mixing temperature of the pentafluorophenyl alkali metal salt with the boron compound, the reaction proceeds extremely slowly at a temperature lower than −100° C., hence a temperature higher than this is desirable, and, if it is higher than 0° C., side reactions proceed extremely rapidly, thus resulting in very low yield in both cases. Hence a temperature lower than this is desirable.

Also, if the temperature is higher than 0° C., then the unreacted pentafluorophenyl alkali metal salt decomposes, hence, reacting at −100° to 0° C. is desirable.

The invention provides a method of producing tetrakis(pentafluorophenyl)borate derivatives, being an important intermediate of a cocatalyst on preparing the catalyst for cationic complex polymerization, in high yield via pentafluorophenyl alkali metal salt not from bromopentafluorobenzene but from more inexpensive pentafluorobenzene. In this respect, the effect of the invention is tremendous.

The invention is illustrated below in more detail in the examples, but the invention is not intended to be restricted thereto.

The yield of a reaction is a value obtained by quantitatively determining the amount of tetrakis(pentafluorophenyl)borate derivatives produced by means of $^{19}F$ NMR using pentafluorotoluene as an internal standard material, or by calculating on the basis of dried weight of crystals after derived to N,N-dimethylanilinium or tributylammonium tetrakis(pentafluorophenyl)borate by cation exchanging with N,N-dimethylanilinium chloride or tributylammonium chloride. The purity was determined by means of $^{19}F$ NMR using pentafluorotoluene as an internal standard material.

EXAMPLE 1

A 100 ml volume glass three-neck flask was equipped with a 50 ml volume glass dropping funnel, temperature resistor and septum rubber and the inside of the system was sufficiently replaced with nitrogen. Into the flask, 5 g (29.8 mmol) of pentafluorobenzene and 30 ml of diethyl ether were charged. and the solution was cooled to −65° C.

Thereafter, a 16.1 wt. % pentans solution (12.3 g, 29.8 mmol) of tert-butyllithium charged into the dropping funnel was added dropwise while not allowing the inner temperature to exceed −55° C. After the completion of dropwise addition, the reaction mixture was stirred at −65° to −55° C. to prepare pentafluorophenyllithium.

To the solution of pentafluorophenyllithium thus prepared was added 1 mol/L hexane solution (7.45 mL, 7.45 mmol) of boron trichloride at −65° to −55° C., and the mixture was stirred for 30 minutes at the same temperature. Then, the temperature was raised to room temperature, diethyl ether was removed by distillation from the reaction mixture, and the organic layer was washed thrice with 20 mL of water. After combining the aqueous layers, 1.1 equivalent to the boron source of an aqueous solution of N,N-dimethylanilinium chloride was reacted with the aqueous layer to deposit white crystals. The crystals obtained were filtered, washed with water and then dried under vacuum to obtain N,N-dimethylanilinium tetrakis(pentafluorophenyl)borate in 92.3% yield. When determining the purity by means of $^1H$ and $^{19}F$ NMR using pentafluorotoluene as an internal standard material, it showed 98 wt. % or higher.

EXAMPLE 2

To a solution of pentafluorobenzene (4.40 g, 26.2 mmol) and diethyl ether (50 ml) was added dropwise a 20 wt. % tertbutyllithium/pentane solution (7.98 g, 25.0 mmol) while Keeping the temperature of the reaction mixture at −55° to −65 ° C., and, after the completion of dropwise addition, the mixture was stirred for about 0–5 hours while keeping the temperature at −25° to −50 ° C. Thereafter, a 20.0 wt. % tris(pentafluorophenyl)borane/toluene solution ( 63.8 g, 25.0 mmol) was mixed while keeping the temperature of the reaction mixture at −25° to −40° C., which was stirred for 30 minutes at the same temperature and then the temperature was raised to room temperature. From the solution of lithium tetrakis(pentafluorophenyl)borate thus obtained, diethyl ether was removed by distillation and the organic layer was washed thrice with 20 mL of water. After combining the aqueous layers, 1.1 equivalent to the boron source of aqueous solution of N,N-dimethylanilinium chloride was reacted with the aqueous layer to deposit white crystals. The crystals obtained were filtered, washed with water and then dried under vacuum to obtain N,N-dimethylanilinium tetrakis(pentafluorophenyl)borate in 97.3% yield. When determining the purity by means of $^1$H and $^{19}$F NMR using pentafluorotoluene as an internal standard material, it showed 98% or higher.

EXAMPLE 3

To a solution of pentafluorobenzene (4.40 g, 26.2 mmol) and diethyl ether (50 ml) was added dropwise a 20 wt. % sec-butyllithium/hexane solution ( 7.98 g, 25.0 mmol) while keeping the temperature of the reaction mixture at −55° to −65 ° C., and, after the completion of dropwise addition, the mixture was stirred for about 0.5 hours while keeping the temperature at −25°–50° C. Thereafter, a 20.0 wt. % tris(pentafluorophenyl)borane/toluene solution ( 63.8 g, 25.0 mmol was mixed while keeping the temperature of the reaction mixture at −25° to −40° C., which was stirred for 30 minutes at the same temperature and then the temperature was raised to room temperature. From the solution of lithium tetrakis(pentafluorophenyl)borate thus obtained, diethyl ether was removed by distillation and the organic layer was washed thrice with 20 mL of water. After combining the aqueous layers, 1.1 equivalent to the boron source of an aqueous solution of N,N-dimethylanilinium chloride was reacted with the aqueous layer to deposit white crystals. The crystals obtained were filtered, washed with water and then dried under vacuum to obtain N,N-dimethuylanilinium tetrakis(pentafluorophenyl)borate in 96.1% yield. When determining the purity by means of $^1$H and $^{19}$F NMR using pentafluorotoluene as an internal standard material, it showed 98% or higher.

EXAMPLE 4

A 100 ml volume glass three-neck flask was equipped with a 50 mol volume glass dropping funnel, temperature resistor and septum rubber and the inside of the system was sufficiently replaced with nitrogen. Into the flask. 5 g (29.8 mmol) of pentafluorobenzene and 30 ml of diethyl ether were charged, and the solution was cooled to −65° C.

Thereafter, a 16.1 wt. % pantene solution (12.3 g, 29.8 mmol) of tert-butyllithium charged into the dropping funnel was added dropwise while not allowing the inner temperature to exceed −55° C. After the completion of dropwise addition, the reaction mixture was starred at −65° to −55° C. to prepare pentafluorophenyllithium.

To the solution of pentafluorophenyllithium thus prepared was added 1 mol/L hexane solution (7.45 mL, 7.45 mmol) of boron trichloride at −65° to −55° C., and the mixture was stirred for 30 minutes at the same temperature, Then, the temperature was raised to room temperature and lithium chloride produced as a by-product was filtered off. When determining the solution of lithium tetrakis(pentafluorophenyl)borate obtained by means of $^{19}$F NMR using pentafluorotoluene as an internal standard material, the yield was 94.3%.

EXAMPLE 5

After a solution of pentafluorobenzene (15.8 g, 100.0 mmol) and diethyl ether (100 ml) was cooled to −40° C., a 25 wt. % tert-butyllithium/pentane solution (22.5 g, 88.0 mmol) was added and the mixture was stirred for 22 hours at −30° to −40° C. Thereafter, 1.0 mol/L boron trichloride/hexane solution (21.0 ml, 21.0 mmol) was added at −40° C. and the temperature was raised to room temperature over 2 hours. From the solution of lithium tetrakis(pentafluorophenyl)borate thus obtained, diethyl ether was removed by distillation and the organic layer was washed thrice with 30 mL of water. After combining the aqueous layers, 1.1 equivalent to the boron source of an aqueous solution of tributylammonium chloride was reacted with the aqueous layer to deposit white crystals. The crystals obtained were filtered, washed with water and then dried under vacuum to obtain tributylammonium tetrakis(pentafluorophenyl)borate in 95.2% yield. When determining the purity by means of $^1$H and $^{19}$F NMR using pentafluorotoluene as an internal standard material, it showed 98 wt. % or higher.

EXAMPLE 6

After a solution of pentafluorobenzene (14.8 g, 88.0 mmol) end diethyl ether (100 ml) was cooled to −40° C., a 20 wt. % butyllithium/hexane solution (28.1 g, 87.7 mmol) was added and the mixture was stirred for 10 hours at −30° to −40 ° C. Thereafter, boron trifluoride-diethyl ether complex (2.84 g, 20.0 mmol) was added at −40° C. and the temperature was raised to room temperature over 2 hours. After stirring overnight at room temperature, toluene (200 ml) was added and, after distilling off diethyl ether and hexane under heat, toluene was also distilled off further under heat to an extent of recovering about 30% of the added amount. After filtering off precipitated lithium fluoride, toluene was removed to bone-dry to obtain lithium tetrakis(pentafluorophenyl)borate in 51% yield.

EXAMPLE 7

After a solution of pentafluorobenzene (14.8 g, 88.0 mmol) and diethyl ether (100 ml) was cooled to −40° C., a 24 wt. % tert-butyllithium/pentane solution (23.4 g, 87.7 mmol) was added and the mixture was stirred for 10 hours at −30° to −40° C. Thereafter, boron trifluoride-diethyl ether complex (2.84 g, 20.0 mmol) was added at −40° C. and the temperature was raised to room temperature over 2 hours. After stirring overnight at room temperature, toluene (200 ml) was added, and after distilling off diethyl ether and pentane under heat, toluene was also distilled off further under heat to an extent of recovering about 30% of the added amount. After filtering off precipitated lithium fluoride, toluene was removed to bone-dry to obtain lithium tetrakis(pentafluorophenyl)borate in 68% yield.

EXAMPLE 8

After a solution of pentafluorobenzene (15.1 g, 90.0 mmol) and diethyl ether (100 ml) was cooled to −40° C., a 20 wt. % sec-butyllithium/hexane solution (28.2 g, 88.0 mmol) was added and the mixture was stirred for 10 hours at −30° to −40° C. Thereafter, boron trifluoride-diethyl ether complex (2.84 g, 20.0 mmol) was added at −40° C. and the temperature was raised to room temperature over 2 hours. After stirring overnight at room temperature, toluene (200 ml) was added and, after distilling off diethyl ether and hexane under heat, toluene was also distilled off further under heat to an extent of recovering about 30% of the added amount. After filtering off precipitated lithium fluoride, toluene was removed to bone-dry to obtain lithium tetrakis(pentafluorophenyl)borate in 65% yield.

EXAMPLE 9

After a solution of pentafluorobenzene (14.8 g. 88.0 mmol) and diethyl ether (100 ml) was cooled to −40° C., a 15 wt. % butylsodium/hexane solution (47.0 g, 88.0 mmol) was added and the mixture was stirred for 1 hour at −30° to −40 ° C. Thereafter, boron trifluoride-diethyl ether complex (2.84 g, 20.0 mmol) was added at −40° C. and the temperature was raised to room temperature over 2 hours. From the solution of sodium tetrakis(pentafluorophenyl)borate thus obtained, diethyl ether was removed by distillation and the organic layer was washed thrice with 20 mL of water. After combining the aqueous layers, 1.1 equivalent to the boron source of an aqueous solution of N,N-dimethylanilinium chloride was reacted with the aqueous layer to deposit white crystals. The crystals obtained were filtered, washed with water and then dried under vacuum to obtain N,N-dimethylanilinium tetrakis(pentafluorophenyl)borate in 86.1% yield. When determining the purity by means of $^1$H and $^{19}$F NMR using pentafluorotoluene as an internal standard material, it showed 98 wt. % or higher.

EXAMPLE 10

After a solution of pentafluorobenzene (16.8 g, 100.0 mmol) and dibutyl ether (100 ml) was cooled to −40° C., a 20 wt. % sec-butyllithium/hexane solution (28.2 g, 88.0 mmol) was added and the mixture was stirred for 2 hours at −30° to −40° C. Thereafter, boron trifluoride-diethyl ether complex (2.84 g, 20.0 mmol) was added at −40° C. and the temperature was raised to room temperature over 2 hours. After stirring overnight at room temperature, octane (200 ml) was added and, after distilling off diethyl ether and hexane under heat, octane was also distilled off further under heat to an extent of recovering about 30% of the added amount. After filtering off precipitated lithium fluoride, octane was removed to bone-dry to obtain lithium tetrakis(pentafluorophenyl)borate in 67.3% yield.

EXAMPLE 11

After a solution of pentafluorobenzene (14.8 g, 88.0 mmol) and diisopropyl ether (100 ml) was cooled to −40° C., a 18 wt. % sec-butyllithium/hexane solution (31.3 g, 88.0 mmol) was added and the mixture was stirred for 0.5 hours at −30° to −40° C. Thereafter, 1 mol/L boron trichloride/hexane solution (20 mL, 20.0 mmol) was added at −40° C. and the temperature was raised to room temperature over 2 hours. From the solution of lithium tetrakis(pentafluorophenyl)borate thus obtained, diisopropyl ether was removed by distillation and the organic layer was washed thrice with 20 mL of water. After combining the aqueous layers, 1.1 equivalant to the boron source of an aqueous solution of N,N-dimethylanilinium chloride was reacted with the aqueous layer to deposit white crystals. The crystals obtained were filtered, washed with water and then dried under vacuum to obtain N,N-dimethylanilinium tetrakis(pentafluorophenyl)borate in 95.1% yield. When determining the purity by means of $^1$H and $^{19}$F NMR using pentafluorotoluene as an internal standard material, it showed 98 wt. % or higher.

EXAMPLE 12

After a solution of pentafluorobenzene (14.8 g, 88.0 mmol) and diethyl ether (100 ml) was cooled to −40° C. a 15 wt. % tert-butyllithium/pentane solution was added and the mixture was stirred for 30 hours at −30° to −40° C. Thereafter, trimethyl borate (2.08 g. 20.0 mmol) was added at −40 ° C. and the temperature was raised to room temperature over 2 hours. After stirring overnight at room temperature, octane (200 ml) was added. Then, diethyl ether was removed by distillation and the organic layer was washed thrice with 20 mL of water. After combining the aqueous layers, 1.1 equivalent to the boron source of an aqueous solution of N,N-dimethylanilinium chloride was reacted with the aqueous layer to deposit white crystals. The crystals obtained were filtered, washed with water and then dried under vacuum to obtain N,N-dimethylanilinium tetrakis(pentafluorophenyl)borate in 83.2% yield. When determining the purity by means of $^1$H and $^{19}$F NMR using pentafluorotoluene as an internal standard material, it showed 98 wt. % or higher.

What is claimed is:

1. A method of producing tetrakis(pentafluorophenyl)borate of the molecular formula $$(C_6F_5)_4BM \qquad (VII),$$

wherein M denotes an alkali metal ion, comprising reacting 1 equivalent of pentafluorobenzene of the following formula $$C_6HF_5 \qquad (I),$$

with 0.5 to 1.5 equivalents of organometallic compound represented by the formula $$RM \qquad (II),$$

wherein M denotes an alkali metal ion, R denotes a hydrocarbon group with carbon atoms of 1 to 10 and the said hydrocarbon group may contain functional groups having no influence on the reaction, at a temperature in the range of −120° to 80° C., in an ether type solvent, a hydrocarbon type solvent or a mixture of the ether type solvent with the hydrocarbon type solvent, to generate pentafluorophenyl alkali metal salt represented by the formula $$C_6F_5M \qquad (III),$$

wherein M denotes an alkali metal ion, and, then, reacting 1 equivalent of a boron compound represented by the formula $$BX_3 \qquad (IV),$$

wherein X denotes a halogen atom, a substituent of the formula $$OR \qquad (V),$$

wherein R denotes a hydrocarbon group with carbon atoms of 1 to 10 and the said hydrocarbon may contain functional groups having no influence on the reaction, or a substituent represented by the formula $$NR'R'' \qquad (VI),$$

wherein R' and R" denote identically or differently hydrogen atoms or hydrocarbon groups with carbon atoms of 1 to 20, wherein said hydrocarbon group may contain functional groups having no influence on the reaction and R' and R" may link one another to form a ring, and may form 1:1 complex with the ether type solvent, with not less than 3.7 equivalents of pentafluorophenyl metal compound of the formula (III).

2. A method of producing tetrakis(pentafluorophenyl)borate derivatives of the formula $$(C_6F_5)_4BM \qquad (VII),$$

comprising preparing a pentafluorophenyl alkali metal salt of the formula $C_6F_5M$ (III) in the manner set forth in claim 1, and, reacting 1 equivalent of tris(pentafluorophenyl)borane of the formula $$(C_6F_5)_3B \qquad (VIII),$$

with not less than 0.8 equivalents of said pentafluorophenyl metal compound of the formula (III).

* * * * *